US00PP15468P2

(12) United States Plant Patent
Cain et al.

(10) Patent No.: US PP15,468 P2
(45) Date of Patent: Jan. 4, 2005

(54) GRAPEVINE NAMED 'SUGRATWENTYSEVEN'

(50) Latin Name: *Vitis vinifera*
Varietal Denomination: Sugratwentyseven

(75) Inventors: David W. Cain, Bakersfield, CA (US); Michael J. Striem, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 10/618,503

(22) Filed: Jul. 10, 2003

(51) Int. Cl.[7] ..... A01H 5/00
(52) U.S. Cl. ..... Plt./205
(58) Field of Search ..... Plt./205

*Primary Examiner*—Bruce R. Campell
*Assistant Examiner*—Michelle Kizilkaya
(74) *Attorney, Agent, or Firm*—Knobbe, Martens, Olson & Bear, LLP

(57) ABSTRACT

A new and distinct grapevine variety characterized by producing firm and crisp, naturally medium sized, long-elliptic shaped grapes with a black tender skin color. The grapes have an excellent eating quality, having a medium sugar content, high acidity and a aromatic flavor.

1 Drawing Sheet

Latin name of the genus and species claimed: *Vitis vinifera.*
Variety denomination: 'Sugratwentyseven'.

BACKGROUND AND SUMMARY OF THE INVENTION

This invention relates to the discovery and asexual propagation of a new variety of grapevine as herein described and illustrated. The new variety is characterized by possessing firm, crisp, naturally medium-sized black seedless grapes. The grapes are long-elliptic in shape and have a nice aromatic flavor.

The new 'Sugratwentyseven' variety was first hybridized by David W. Cain and Michael J. Striem in Wasco, Kern County, Calif., the variety being originated by controlled hybridization and subsequent ovule culture of seed traces and embryo rescue procedures. The seed parent is the unpatented variety 'Calinda' and the pollen parent is the unpatented variety 'Fantasy'. The parent varieties were first crossed in May 1990, with the date of sowing being August 1990 and the date of first flowering being May 1993. The new 'Sugratwentyseven' variety was first asexually propagated by David W. Cain in January, 1994, in Wasco, Kern County, Calif., using hardwood cuttings.

The new variety 'Sugratwentyseven' is a mid-season ripening black seedless grape, characterized by producing naturally medium-sized grapes that are firm and crisp. The grapes have a black tender skin color, long-elliptic berry shape, medium sugar content, high acidity and a nice aromatic flavor, giving the grapes an excellent eating quality. The new variety 'Sugratwentyseven' ripens about 7–10 days after 'Thompson seedless' grape, when grown in the San Joaquin Valley, Calif. In addition to the exceptional eating qualifications, the grapes also have an outstanding ability to hang on the vine.

'Sugratwentyseven' most nearly resembles its pollen parent, 'Fantasy' variety in its berry shape, skin coloration and ripening time. It is distinguished from 'Fantasy' and other commonly grown black seedless grapevine varieties by possessing a very firm and crisp flesh, a thin skin with a pleasant aromatic flavor, which gives it an exceptional eating quality. The vine is less vigorous and more productive than the vine of 'Fantasy'. The new grapevine variety cv. 'Sugratwentyseven' is also distinguished from 'Fantasy' in that it bears naturally larger and elliptic berries, with much better hanging ability on the vine.

'Sugratwentyseven' is distinguished from other commonly grown black seedless grapes, such as 'Sugrasixteen'. The new grapevine variety resembles the 'Sugrasixteen' grapevine variety by berry shape and color. It can be distinguished from the 'Sugrasixteen' variety by having a mild aromatic flavor (rather than a muscat flavor). Additionally, the new variety 'Sugratwentyseven' possesses grapes having a firm and crisp flesh, thin skin and a substantially longer hanging ability on the vines, as compared with 'Sugrasixteen'.

The new 'Sugratwentyseven' variety has been shown to maintain its distinguishing characteristics through successive asexual propagations by, for example, cuttings.

BRIEF DESCRIPTION OF THE FIGURE

The accompanying photographic illustration in

DETAILED BOTANICAL DESCRIPTION OF THE INVENTION

Figure 1:
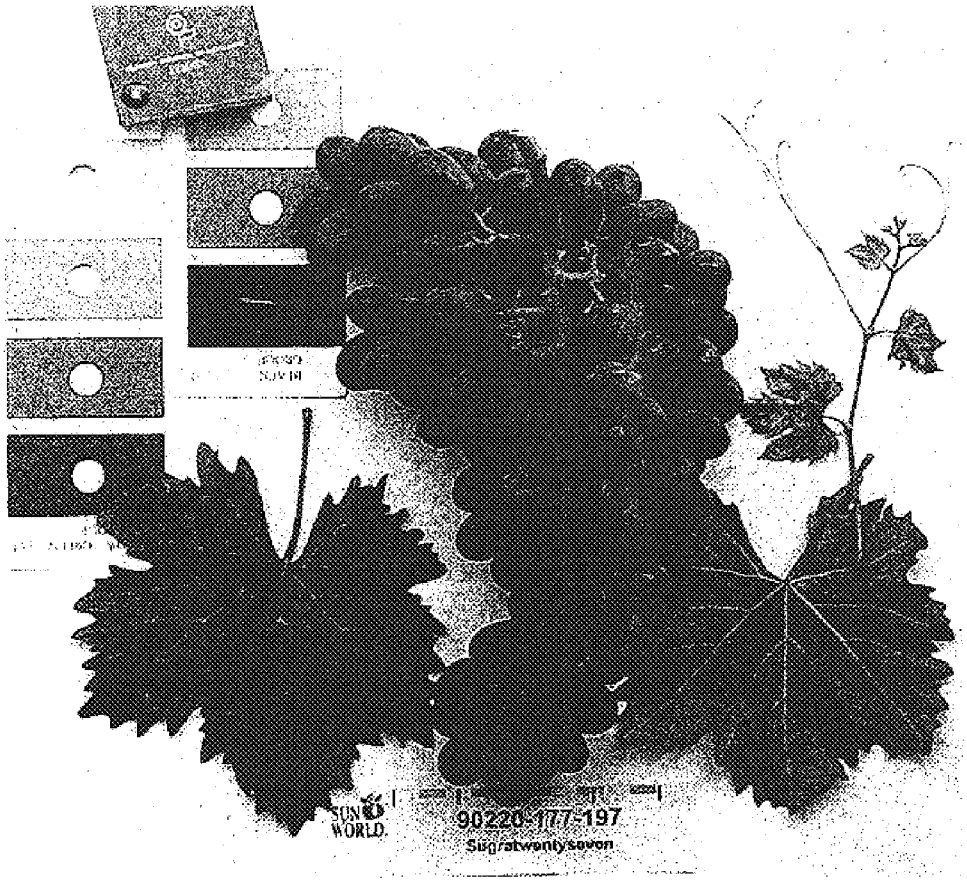
FIG. 1 illustrates in full color a typical cluster of berries, a young shoot, and a mature leaf blade of the new grapevine. The colors are as nearly true as is reasonably possible in a color representation of this type.

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (*Vitis* spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugratwentyseven' plants grown in the vicinity of Wasco, Kern County, Calif., during 2002, and is believed to apply to plants of the variety grown under similar conditions of soil and climate elsewhere.

VINE

General:
*Size.*—Medium.
*Vigor.*—Vigorous.
*Density of foliage.*—Medium.
*Productivity.*—Productive.
*Root stock.*—Own roots.
Trunk:
*Shape.*—Stocky.
*Straps.*—Split.
*Surface texture.*—Smooth.
*Inner bark color.*—About Greyed-orange 165A.

SHOOTS

Young shoot:
*Form of tip.*—Closed.
*Distribution of anthocyanin coloration of tip.*—Absent.
*Intensity of anthocyanin coloration of tip.*—Absent.
*Density of prostrate hairs on tip.*—Sparse.
*Density of erect hairs on tip.*—Absent.
Woody shoot (mature cane):
*Shape.*—Medium.
*Internode length.—Long — approximately* 38.06 mm.
*Width at node.*—Approximately 15.95 mm.
*Cross section.*—Elliptic.
*Surface.*—Ribbed.
*Main color.*—About Greyed-orange 166B.
*Lenticels.*—Absent.
*Density of erect hairs on nodes.*—None or very sparse.
*Density of erect hairs on internodes.*—None or very sparse.
*Growth of axillary shoots.*—Strong — approximately 40.19 cm.
Flowering shoot:
*Vigor during flowering.*—Strong.
*Attitude during flowering on shoots which are not tied.*—Erect.
*Color of dorsal side of internodes.*—About Yellow-green 144A.
*Color of ventral side of internodes.*—About Yellow-green 144A.
*Color of dorsal side of nodes.*—About Yellow-green 144A.
*Color of ventral side of nodes.*—About Yellow-green 144A.
*Density of erect hairs on nodes.*—Very sparse.
*Erect hairs on internode.*—Present.
*Density of prostrate hairs on nodes.*—Very sparse.
*Density of prostrate hairs on internodes.*—Very sparse.
*Anthocyanin coloration of buds.*—Absent or very weak.
Tendrils:
*Distribution on the shoot at full flowering.*—Discontinuous.
*Thickness.*—Thin.
*Color.*—About Yellow-green 144A.
*Form.*—Trifurcated.
*Number of consecutive tendrils.*—Up to two.
*Length of tendril.*—Medium — approximately 21 cm.

LEAVES

Young leaves:
*Color of upper surface of first 4 distal unfolded leaves.*—Yellow with bronze spots.
*Average intensity of anthocyanin coloration of six distal leaves prior to flowering.*—Absent or very weak.
*Density of prostrate hairs between veins at lower surface of 4th distal unfolded leaf.*—Absent.
*Density of erect hairs between veins at lower surfaces of 4th distal unfolded leaf.*—Absent.
*Density of prostrate hairs on veins at lower surface of 4th distal unfolded leaf.*—Absent.
*Density of erect hairs on veins at lower surface of 4th distal unfolded leaf.*—Absent.
Mature leaves:
*Average length.*—Approximately 95 mm.
*Average width.*—Approximately 134 mm.
*Size of blade.*—Medium.
*Shape of blade.*—Pentagonal.
*Number of lobes.*—Five.
*Anthocyanin coloration of main veins on the upper side of the blade.*—Absent.
*Mature leaf profile.*—Revolute.
*Blistering surface of blade upper surface.*—Absent.
*Leaf blade tip.*—In the plane of the leaf.
*Undulation of margin.*—Slight.
*Apex.*—Cuspidate.
*Thickness.*—Thin.
*Undulation of blade between main and lateral veins.*—Absent.
*Shape of teeth.*—Mixture of both sides straight and both sides convex.
*Length of teeth.*—Medium.
*Ratio length/width of teeth.*—Medium.
*General shape of petiole sinus.*—Half open.
*Tooth at petiole sinus.*—Absent.
*Petiole sinus limited by veins.*—Absent.
*Shape of upper lateral sinus.*—Open.
*Depth of upper lateral sinus.*—Shallow.
*Density of prostrate hairs between veins on lower surface of blade.*—Absent.
*Density of erect hairs between veins on lower surface of blade.*—Absent.
*Density of prostrate hairs on main veins on lower surface of blade.*—None or very sparse.
*Density of erect hairs on main veins on lower surface of blade.*—None or very sparse.
*Density of prostrate hairs on main veins on upper surface of blade.*—Absent.
*Autumn coloration of leaves.*—About Yellow-green 153B.
Upper surface:
*Color.*—About Yellow-green 147B.
*Surface texture.*—Smooth.
*Surface appearance.*—Semi-glossy.
*Goffering of blade.*—Present.
Lower surface:
*Color.*—About Yellow-green 146A.
*Anthocyanin coloration of main veins on lower leaf surface.*—Absent.
*Glossiness.*—Weak.
*Pubescence.*—Absent.

*Surface texture.*—Rugose.
*Surface appearance.*—Dull.

Petiole:
*Length of petiole.*—Medium — approximately 5.2 cm.
*Length of petiole compared to middle vein.*—Much shorter.
*Density of prostrate hairs on petiole.*—Absent.
*Density of erect hairs on petiole.*—Absent.
*Shape of base of petiole sinus.*—V-shaped.

Buds:
*Shape.*—Pointed.
*Size.*—Medium — approximately 3 mm length by 5 mm width.
*Position.*—Slightly held out — approximately at a 45° angle.
*Cane bud fruitfulness.*—Basal mostly fruitful.
*Time of bud burst.*—Medium.

FLOWERS

General:
*Flower sex.*—Hermaphrodite.
*Length of first inflorescence.*—Medium.
*Position of first flowering node.*—Fifth node.
*Number of inflorescences per shoot.*—Approximately 1 to 2.
*Date of full bloom.*—May 9, 2002.
*Time of bloom.*—Medium.
*Size* (*diameter of fully open flower*).—Medium.

FRUIT

General:
*Ripening period.*—Medium — approximately 7 days after Thompson Seedless variety.
*Use.*—Fresh market.
*Keeping quality.*—Good.
*Resistance.*—Insects: medium. Diseases: medium.
*Shipping quality.*—Medium.
*Date of first harvest.*—Aug. 8, 2002.
*Solids-sugar.*—Medium (approximately 18%).
*Refractometer test.*—Approximately 17.6.
*Acid.*—Approximately 6.41 g/l tartaric acid.
*Juice pH.*—Approximately 3.8.

Cluster:
*Bunch size* (*peduncle excluded*).—Large.
*Bunch length* (*peduncle excluded*).—Long — approximately 24.1 cm.
*Bunch width.*—Approximately 14.7 cm.
*Bunch weight.*—Approximately 687 g.
*Bunch density.*—Medium.
*Number of berries.*—Approximately 162.
*Form.*—Cylindrical.

Peduncle:
*Length of peduncle.*—Medium — approximately 53.8 mm.
*Lignification of peduncle.*—Weak.
*Color.*—About Yellow-green 146B.

Berry:
*Size.*—Large.
*Uniformity of size.*—Uniform.
*Berry weight.*—Approximately 5.05 g.
*Shape.*—Broad-elliptic.
*Presence of seeds.*—Rudimentary — approximately 3.7 mg.
*Cross section.*—Circular.
*Dimensions.*—Approximately 26.55 mm longitudinal axis by approximately 18.06 mm horizontal axis.
*Skin color* (*without bloom*).—About Black 202A.
*Coloration of flesh.*—Transparent greenish.
*Juiciness of flesh.*—Slightly juicy.
*Berry firmness.*—Firm.
*Particular flavor.*—None.
*Bloom* (*cultivar wax*).—Medium.
*Pedicel length.*—Short — approximately 6.46 mm.
*Berry separation from pedicel.*—Medium.
*Visibility of hilum.*—Slightly clear.

Skin:
*Thickness.*—Medium.
*Texture.*—Medium.
*Reticulation.*—Absent.
*Roughness.*—Absent.
*Tenacity.*—Free.

What is claimed is:

1. A new and distinct variety of grapevine named 'Sugratwentyseven' as herein illustrated and described.

* * * * *